United States Patent [19]
Arndt et al.

[11] 4,155,915
[45] May 22, 1979

[54] BENZODIOXOLAN DERIVATIVES, PROCESS OF MAKING THE SAME AND HERBICIDAL COMPOSITION CONTAINING SAME

[75] Inventors: Friedrich Arndt; Heinrich Franke, both of Berlin, Fed. Rep. of Germany

[73] Assignee: Schering Aktiengesellschaft, Berlin and Bergkamen, Fed. Rep. of Germany

[21] Appl. No.: 801,739

[22] Filed: May 31, 1977

[30] Foreign Application Priority Data

May 31, 1976 [DE] Fed. Rep. of Germany ....... 2624822

[51] Int. Cl.² ........................................... C07D 317/44
[52] U.S. Cl. .................................. 260/340.5 R; 71/88
[58] Field of Search ...................... 260/340.5 R; 71/88

[56] References Cited

U.S. PATENT DOCUMENTS

| | | | |
|---|---|---|---|
| 2,709,648 | 5/1955 | Ryker et al. | 71/88 X |
| 3,748,331 | 7/1973 | Cooke et al. | 260/340.5 R X |
| 3,859,313 | 1/1975 | Maravetz | 71/88 X |
| 3,997,564 | 12/1976 | Cooke et al. | 260/340.5 |

FOREIGN PATENT DOCUMENTS

436838 11/1967 Switzerland .................................. 71/88

*Primary Examiner*—Ethel G. Love
*Attorney, Agent, or Firm*—Michael J. Striker

[57] ABSTRACT

Benzodioxolan derivatives of the formula

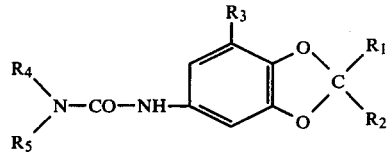

wherein $R_1$ and $R_2$ are the same or different and are hydrogen, an aliphatic hydrocarbon residue, a halogenated aliphatic hydrocarbon residue, an aromatic hydrocarbon residue, a substituted aromatic hydrocarbon residue,
 a heterocyclic residue or a substituted heterocyclic residue,
 or wherein $R_1$ and $R_2$ together with the adjoining carbon atom are a cycloaliphatic hydrocarbon residue which may additionally be substituted by nitrogen or oxygen or both, and wherein $R_3$ is hydrogen or an aliphatic hydrocarbon residue,
 and wherein $R_4$ is a saturated or unsaturated aliphatic hydrocarbon residue or is alkoxy and wherein
 $R_5$ is hydrogen or is a saturated or unsaturated aliphatic hydrocarbon residue. The compounds have a high herbicidal activity against weeds and superior selective herbicidal properties for agricultural and horticultural plantations. The invention also embraces processes for making the compounds and compositions containing the same.

46 Claims, No Drawings

BENZODIOXOLAN DERIVATIVES, PROCESS OF MAKING THE SAME AND HERBICIDAL COMPOSITION CONTAINING SAME

BACKGROUND OF THE INVENTION

The invention relates to novel benzodioxolan derivatives.

It is known that certain urea derivatives, for instance 1-(4-chlorophenyl)-3,3-dimethylurea or 1-(3,4-dichlorophenyl)-3,3-dimethylurea may be used as herbicidal compounds for total destruction of weeds (U.S. Pat. No. 2,655,445). These compounds, because of their low selectivity, are however little suited to suppress weeds in agricultural plantations.

It is futhermore known to employ urea derivatives, for instance 1-[4-(4-chlorophenoxy)-phenyl]-3,3-dimethylurea as selective herbicidal compounds (German Pat. No. 1,142,251). This compound, however, has only a relatively limited herbicidal action and is therefore hardly ever used in agricultural plantations. This compound, in addition, has the drawback of a rather limited applicability since it must be applied about between the second and twelfth day after seeding out the plant, that is prior to emergence of the weeds.

It is therefore the object of the present invention to provide for a herbicidal compound which both has a high herbicidal activity against weeds, and a superior herbicidal activity in agricultural and horticultural plantations.

SUMMARY OF THE INVENTION

This object is met by a benzodioxolan derivative of the formula

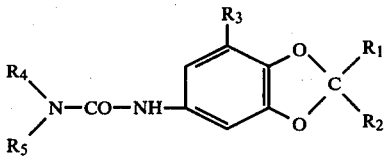

I in which $R_1$ and $R_2$ are the same or different and are hydrogen, an aliphatic hydrocarbon residue, a halogenated aliphatic hydrocarbon residue, an aromatic hydrocarbon residue, a substituted aromatic hydrocarbon residue, a heterocyclic residue or a substituted heterocyclic residue, or wherein $R_1$ and $R_2$ together with the adjoining carbon atom are a cycloaliphatic hydrocarbon residue which may additionally be substituted by nitrogen or oxygen or both, and wherein $R_3$ is hydrogen or an aliphatic hydrocarbon residue, and wherein $R_4$ is a saturated or unsaturated aliphatic hydrocarbon residue or is alkoxy and wherein $R_5$ is hydrogen or is a saturated or unsaturated aliphatic hydrocarbon residue. The compounds have a high herbicidal activity against weeds and superior selective herbicidal properties for agricultural and horticultural plantations.

Among these benzodioxolan derivatives superior herbicidal activity have those compounds in which, in the formula I above, $R_1$ and $R_2$ are hydrogen, alkyl of 1 to 9 carbon atoms, monohaloalkyl of 1 to 3 carbon atoms, dihaloalkyl of 1 to 3 carbon atoms, phenyl, or phenyl, pyridyl, or furyl, which three are substituted in one or two places by methyl, halogen, cyano or methoxy, or wherein $R_1$ and $R_2$ together with the adjoining carbon atom form a cycloaliphatic hydrocarbon residue of 5 to 6 carbon atoms, and wherein $R_3$ is hydrogen or methyl, $R_4$ is alkyl of 1 to 4 carbon atoms, alkenyl of 2 to 4 carbon atoms, alkinyl of 2 to 4 carbon atoms or methoxy, and $R_5$ is hydrogen or methyl.

Most preferred for its properties among these compounds are derivatives of formula I in which $R_1$ is chloromethyl or phenyl, $R_2$ is methyl, $R_3$ is hydrogen, $R_4$ is methyl and $R_5$ is hydrogen or methyl.

The benzodioxolan derivatives of the invention are particularly suited for their action against monocotyl or dicotyl weeds as for instance Stellaria m., Senecio v., Matricaria ch., Lamium a., Centaurea c., Amaranthus r., Galium a., Chrysanthemum, Echinochloa cg, Setaria i., Digitaria s., Poa a.

The compounds can be used in agricultural and horticultural plantations, for instance in plantations where alfalfa, bush beans, cotton, soybeans, potatoes, peas, peanuts, maize, grains, rice, onions, carrots, celery, strawberries and decorative plants have been planted.

The amounts applied depend on the specific purpose. They may be between 0.5 and 5 kg of active agent per about 2.5 acres. With higher amounts it is also possible to obtain a total destruction of all weeds. The use can be effected by preemergence and postemergence application.

DETAILS OF THE INVENTION AND PREFERRED EMBODIMENTS

The compounds of the invention can either be used alone or intermixed with each other or in mixture with other active agents. Depending on the purpose, for instance, the following herbicidal agents may be mixed with the compounds of the invention and, if desired, such mixture may be effected only immediately prior to application:

substituted anilines,
substituted aryloxycarboxylic acids and their salts, esters and amides,
substituted ethers,
substituted arsonic acids and their salts, esters and amides,
substituted benzimidazoles,
substituted benzisothiazoles,
substituted benzthiadiazinone dioxides,
substituted benzoxazines,
substituted benzoxazinones,
substituted benzthiazoles,
substituted benzthiadiazoles,
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkyl-thio- or dithiophosphates
substituted quinazolines,
substituted cycloalkylamidocarbonylthiol acids and their salts, esters and amides,
substituted cycloalkylcarbonylamido-thiazoles,
substituted dicarboxylic acids and their salts, esters and amides,
substituted dihydrobenzofuranylsulfonates,
substituted disulfides,
substituted dipyridylium salts,
substituted dithiocarbamates, substituted dithiophosphoric acids and their salts, esters and amides,
substituted urea derivatives,
substituted hexahydro-1H-carbothioates,
substituted hydantoines,
substituted hydrazides,
substituted hydrazonium salts,
substituted isoxazolpyrimidones,
substituted imidazoles,
substituted isothiazolpyrimidones,
substituted ketones,
substituted naphthoquinones,
substituted aliphatic nitriles,
substituted aromatic nitriles,
substituted oxadiazoles,
substituted oxadiazinons,
substituted oxadiazolidindiones,
substituted oxadiazinediones,
substituted phenols and their salts and esters,
substituted phosphonic acids and their salts, esters and amides,
substituted phosphoniumchlorides,
substituted phosphonalkylglycines,
substituted phosphites,
substituted phosphoric acids and their salts, ester and amides,
substituted piperidines,
substituted pyrazoles,
substituted pyrazolalkylcarboxylic acids and their salts, esters, and amides,
substituted pyrazolium salts,
substituted pyrazoliumalkylsulfates,
substituted pyridazines,
substituted pyrimidines,
substituted pyrrolidones,
substituted pyridazones,
substituted pyridine-carbonic acids and their salts, esters and amides,
substituted pyridines,
substituted pyridinecarboxylates,
substituted pyridinone,
substituted pyrimidone,
substituted pyrrolidine-carboxylic acids and their salts, esters and amides,
substituted pyrrolidines,
substituted arylsulfonic acids and their salts, esters and amides,
substituted styrenes,
substituted tetrahydro-oxadiazindiones,
substituted tetrahydromethanoindenes,
substituted tetrahydro-diazol-thiones,
substituted tetrahydro-thiadiazine-thiones,
substituted tetrahydro-thiadiazolediones,
substituted thiadiazoles,
substituted aromatic thiocarboxylic acid amides,
substituted thiocarboxylic acids and their salts, esters and amides,
substituted thiolcarbamates,
substituted thiophosphoric acids and their salts, esters and amides,
substituted triazines,
substituted triazoles
substituted uracils, and
substituted urethidindiones.

It is also possible to use other additives, for instance, non-phytotoxic agents which in herbicides result in a synergistic increase of activity as for instance wetting agents, emulsifying agents, solvents and oily additives.

The compounds of the invention and their mixture are preferably used in the form of overall compositions such as powders, dusting agents, granulates, solutions, emulsions or suspensions. The compositions should include a liquid and/or solid carrier material or diluents and, if desired, wetting, adhesion promoting, emulsifying and/or dispersion agents.

Suitable liquid carrier materials are, for instance, water, aliphatic and aromatic hydrocarbons, such as benzene, toluene, xylene, cyclohexanone, isophorone, dimethylsulfoxide, dimethylformamide, and furthermore mineral oil fractions.

Solid carrier materials are, mineral earths, for instance tonsil, silica gel, talcum, kaolin, attaclay, limestone, silicic acid and plant products, for instance flours.

There may also be added surface active agents, such as, for instance calciumlignosulfonate, polyoxyethylenealkylphenylether, naphthalene-sulfonic acids and their salts, phenolsulfonic acid and their salts, formaldehyde condensation products, fatty alcoholsulfates as well as substituted benzosulfonic acids and their salts.

The amount of the active agent or agents in the compositions can be varied widely. For instance, the compositions may contain between about 10 and 80% by weight of active agents, about 90 to 20% by weight of liquid or solid carrier materials and, if desired, up to 20% by weight of surface active agents.

The application of the compounds can be effected in conventional manner, for instance, by using water as the carrier liquid in spray amounts of about 100 to 1000 liter to about 2.5 acres.

An application of the compounds is possible both in the so-called "low-volume" and "ultra-low-volume" process as also in the form of so-called microgranulates.

PROCESS OF MAKING

The benzodioxolan derivatives of the invention can be made by various processes.

I. Compounds of the formula

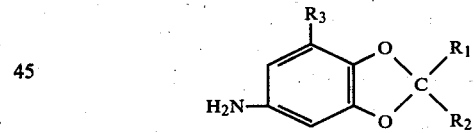

may be reacted with carbamic acid halides of the formula

wherein $R_1$ to $R_5$ are the same as in formula I above, and Hal is halogen. The reaction may be carried out in the presence of a solvent and of an acid acceptor.

II. If $R_5$ in the final compound is to be hydrogen, the compound of formula

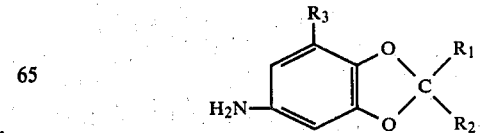

may also be reacted with an isocyanate of the formula

R$_4$-N=C=O

The reaction may be carried out by using a solvent and in the presence of a catalyst. R$_1$ to R$_4$ again has the meaning as in formula I above.

III. A compound of the formula

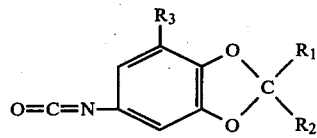

may be reacted with an amine of the formula

and the reaction may be carried out by using a solvent and in the presence of a catalyst. The groups R$_1$ to R$_5$ have again the meaning as in formula I above.

As solvents there are suited materials which are inert to the reaction components, such as, aliphatic and aromatic hydrocarbons as, for instance, hexane, benzene and toluene, chlorinated hydrocarbons, as for instance methylene chloride, chloroform, carbontetrachloride and dichloroethane, ethers, as for instance diethylether, tetrahydrofuran and dioxane, ketones, as for instance acetone and butanone, nitriles, as for instance acetonitrile, and amides, as for instance dimethylformamide and hexamethylphosphoric acid triamide.

As acceptors for the halogen acid are suited organic bases such as tertiary amines as for instance triethylamine, pyridine and dimethylaniline. Used at a large excess these compounds can also simultaneously serve as solvents. Other suitable acid acceptors are inorganic bases such as oxides, hydroxides and carbonates of the alkali and earth alkali metals. As catalysts may be used tertiary amines as for instance triethylamine.

The reaction can be carried out in a temperature range between about −20° and 120° C. Preferred is the range between room temperature and 70° C.

STARTING PRODUCTS

Some of the starting products are benzodioxolamines which are known. These and others can be made according to established procedures. These procedures are for instance:

(a) Pyrocatechol is reacted with an excess of aldehydes or ketones without a solvent at a temperature of 50° to 100° C. in the presence of phosphorus pentoxide.
(b) Pyrocatechol is reacted with aldehydes or ketones in the presence of a strong acid such as sulfuric acid or p-toluene sulfonic acid and the formed water is removed by azeotropic distillation.
(c) Pyrocatechol is reacted with acetals or ketals in the presence of a catalytic amount of an acid, while the alcohol is removed by distillation, or
(d) 2-ethoxy-1,3-benzodioxolane is reacted with aldehydes or ketones without a solvent in the presence of an acid while the formed formic acid ethylester is distilled off.

The thus-obtained benzodioxolans are then nitrated in conventional manner and the resulting nitrocompounds are reduced to the benzodioxolylamines.

EXAMPLES

The following examples further illustrate the compounds of the invention.

EXAMPLE 1

19.5 g (0.1 mol) of 5-amino-2-chloromethyl-2-methyl-1,3-benzodioxolan were dissolved in 100 ml of dry tetrahydrofuran and reacted with 6.3 g (0.11 mol) of methylisocyanate. The solution underwent a rise in temperature without addition of a catalyst. It was subjected to 3 hours of stirring whereupon the excess methyl isocyanate was distilled off together with half of the solvent in a rotary evaporator. The urea derivative crystallized out upon addition of pentane.

There were thus obtained 23 g of 1-(2-chloromethyl-2-methyl-1,3-benzodioxolan-5-yl)-3-methylurea having a melting point of 156° C.

STARTING PRODUCT

The 5-amino-2-chloromethyl-1,3-benzodioxolans employed in this example as starting product was obtained as follows:

A. 2-chloromethyl-2-methyl-1,3-benzodioxolan 110 g (1 mol) of pyrocatechol and 200 ml of chloroacetone were mixed and heated to 50° C. 284 g (2 mol) of phosphoruspentoxide were then added in batches upon strong stirring. The temperature inside the reaction must not exceed 70° C. The mass was then subjected to another hour of stirring whereupon it was decanted and the residue was washed twice with benzene whereupon the united phases were concentrated by evaporation in a rotary evaporator. The mass was then subjected to fractionation in a vacuum (12 torr). The fractions in the boiling range between 104° and 150° C. had a weight of 66 g.

B. 2-chloromethyl-2-methyl-5-nitro-1,3-benzodioxolan 27.7 g (0.15 mol) of the benzodioxolans obtained in Example A were added dropwise at 20° to 35° C. to 100 ml of a 33% nitric acid while stirring strongly. After an hour the solution was poured into ice water and several times extracted with ether. The united ether phases were washed twice with a potassium bicarbonate solution and then with water followed by drying and concentration by evaporation. After addition of hexane the product crystallized out. There were obtained 17 g of crystallized product of a melting point of 72° to 73° C.

C. 2-chloromethyl-2-methyl-5-amino-1,3-benzodioxolan 23 g (0.1 mol) of the nitrocompound obtained as just described were dissolved in 150 ml of ethanol and were then reacted with 2 g of Raney nickel and subsequently with 10 ml (0.2 mol) of hydrazine hydrate. There was a temperature rise and the temperature was then maintained for 1 hour at 60° C. Thereafter another 3 ml of hydrazine hydrate and a little Raney nickel were added and the mass was stirred for another hour at 60° C. It was then permitted to cool off, was filtrated and finally concentrated by evaporation. There remained 19.5 of a brownish oil.

EXAMPLE 2

19.3 g (0.1 mol) of 5-amino-2-phenyl-1,3-benzo-dioxolan were dissolved in 80 ml pyridine and reacted with 12 g (0.11 mol) of dimethylcarbamoylchloride. The solution was subject to a temperature rise. After 3 hours one-half of the pyridine was distilled off in a rotary evaporator and the residue was poured into ice water. Extraction was then effected several times with acetic ester whereupon the combined acetic ester phases were washed with dilute hydrochloric acid and then with water followed by drying and concentration by evaporation.

Crystallization from toluene resulted in 9 g of 1-(2-phenyl-1,3-benzodioxolane-5-yl)-3,3-dimethylurea having a melting point of 128° to 129° C.

STARTING MATERIAL

The 5-amino-2-phenyl-1,3-benzodioxolan used in this example as starting material was obtained as follows:

D. 2-phenyl-1,3-benzodioxolan 110 g (1 mol) of pyrocatechol and 180 g (1 mol) of benzaldehydediethylacetal dissolved in 400 ml toluene were reacted with 1 g of oxalic acid and heated to boiling point. By means of a distillation column, ethanol was continuously distilled off until the temperature at the top of the column had reached 100° C.

After cooling off, the solution was shaken out with a sodium carbonate solution, washed with water, dried and evaporated by concentration. Distillation and a high vacuum (0.05 torr) furnished 63 g of an oil of a boiling point between 80° and 81° C. that solidified in the receiver and then melted at a temperature of 46° to 48° C.

E. 5-nitro-2-phenyl-1,3-benzodioxolan

A solution of 39.6 g (0.2 mol) of the benzodioxolan obtained as just described in 150 ml of acetic acid ester was added dropwise at 25° to 35° C. to 150 ml of a 33% nitric acid. The solution was poured into ice water after 2 hours and then extracted several times with acetic ester. The combined acetic ester phases were then washed several times with a solution of potassium bicarbonate and then with water, followed by drying and evaporation by concentration. Crystallization from ethanol furnished 37 g of a product of the melting point between 84° and 85° C.

F. 5-amino-2-phenyl-1,3-benzodioxolan 24.3 g (0.1 mol) of the nitrocompound obtained in the preceding example dissolved in 200 ml of an equal parts mixture of ethanol and tetrahydrofuran were hydrogenated in an autoclave in the presence of 3 g Raney nickel and further processed in conventional manner.

The following benzodioxolan derivatives were produced in an analogous manner to those in Examples 1 and 2.

| Compound | Physical Constants |
|---|---|
| 1-(2,2-dimethyl-1,3-benzodioxolan-5-yl)-3-methylurea | m.p. 147–148.5° C. |
| 1-(2,2-dimethyl-1,3-benzodioxolan-5-yl)-3,3-dimethylurea | m.p. 152–153° C. |
| 1-(2-ethyl-2-methyl-1,3-benzodioxolan-5-yl)-3,3-dimethylurea | m.p. 132–133° C. |
| 1-(2-ethyl-2-methyl-1,3-benzodioxolan-5-yl-3-methylurea | m.p. 120–121° C. |
| 1-(2-isobutyl-2-methyl-1,3-benzodioxolan-5-yl)-3-methylurea | m.p. 90–92° C. |
| 1-(2-isobutyl-2-methyl-1,3-benzodioxolan-5-yl)-3,3-dimethylurea | m.p. 98–99° C. |
| 1-(1,3-benzodioxolan-(2-spirocyclohexane)-5-yl)-3,3-dimethylurea | m.p. 134–135° C. |
| 1-(1,3-benzodioxolan-(2-spirocyclohexane)-5-yl)-3-methylurea | m.p. 152–154° C. |
| 1-(1,3-benzodioxolan-(2-spirocyclopentane)-5-yl)-3,3-dimethylurea | m.p. 153–155° C. |
| 1-(1,3-benzodioxolan-(2-spirocyclopentane)-5-yl)-3-methylurea | m.p. 145° C. |
| 1-(2,2-diethyl-1,3-benzodioxolan-5-yl)-3-methylurea | m.p. 98–99° C. |
| 1-(2,2-diethyl-1,3-benzodioxolan-5-yl)-3,3-dimethylurea | m.p. 122–123° C. |
| 1-(2-methyl-2-pentyl-1,3-benzodioxolan-5-yl)-3,3-dimethylurea | m.p. 96–97° C. |
| 1-(2-methyl-2-pentyl-1,3-benzodioxolan-5-yl)-3-methylurea | oil |
| 1-(2-isopropyl-1,3-benzodioxolan-5-yl)-3-methylurea | m.p. 123–124° C. |
| 1-(2-isopropyl-1,3-benzodioxolan-5-yl)-3,3-dimethylurea | m.p. 121° C. |
| 1-(2-methyl-2-nonyl-1,3-benzodioxolan-5-yl)-3,3-dimethylurea | m.p. 74° C. |
| 1-(2-methyl-2-nonyl-1,3-benzodioxolan-5-yl)-3-methylurea | m.p. 74–75° C. |
| 1-(2-methyl-2-propyl-1,3-benzodioxolan-5-yl)-3-methylurea | m.p. 89–90° C. |
| 1-(2-methyl-2-propyl-1,3-benzodioxolan-5-yl)-3,3-dimethylurea | m.p. 119–120° C. |
| 1-(2-ethyl-2-methyl-1,3-benzodioxolan-5-yl)-3-ethylurea | m.p. 100–101° C. |
| 1-(2,2-dipropyl-1,3-benzodioxolan-5-yl)-3-methylurea | m.p. 136–137° C. |
| 1-(2,2-dipropyl-1,3-benzodioxolan-5-yl)-3,3-dimethylurea | m.p. 129–131° C. |
| 1-(2,2-dimethyl-1,3-benzodioxolan-5-yl)-3-ethylurea | m.p. 110–111° C. |
| 1-(2,2-dimethyl-1,3-benzodioxolan-5-yl)-3-butylurea | m.p. 125–126° C. |
| 1-(2,2-dimethyl-1,3-benzodioxolan-5-yl)-3-tert.-butylurea | m.p. 152–156° C. |
| 1-(2-isopropyl-2-methyl-1,3-benzodioxolan-5-yl)-3,3-dimethylurea | m.p. 94–96° C. |
| 1-(2-isopropyl-2-methyl-1,3-benzodioxolan-5-yl)-3-methylurea | m.p. 111–113° C. |
| 1-(2-methyl-2-phenyl-1,3-benzodioxolan-5-yl)-3,3-dimethylurea | m.p. 141–142° C. |
| 1-(2-methyl-2-phenyl-1,3-benzodioxolan-5-yl)-3-methylurea | m.p. 130–132° C. |
| 1-(2-chloromethyl-2-methyl-1,3-benzodioxolan-5-yl)-3,3-dimethylurea | m.p. 155–157° C. |
| 1-(2-ethyl-2,7-dimethyl-1,3-benzodioxolan-5-yl)-3,3-dimethylurea | m.p. 106–110° C. |
| 1-(2-ethyl-2,7-dimethyl-1,3-benzodioxolan-5-yl)-3-methylurea | m.p. 109–112° C. |
| 1-(2-chloromethyl-2,7-dimethyl-1,3-benzodioxolan-5-yl)-3-methylurea | m.p. 136–140° C. |
| 1-(2-chloromethyl-2-methyl-1,3-benzodioxolan-5-yl)-3-methoxy-3-methylurea | m.p. 87–88° C. |
| 1-(2-chloromethyl-2-methyl-1,3-benzodioxolan-5-yl)-3-methyl-3-(1-methyl-2-propinyl)-urea | m.p. 138–139° C. |
| 1-(2,2-dimethyl-1,3-benzodioxolan-5-yl)-3-methoxy-3-methylurea | m.p. 73–75° C. |
| 1-(2-phenyl-1,3-benzodioxolan-5-yl)-3-methylurea | m.p. 166–167° C. |
| 1-[2-(4-chlorophenyl-2-methyl-1,3-benzodioxolan-5-yl]-3-methylurea | m.p. 162–163° C. |
| 1-[2-(4-chlorophenyl)-2-methyl-1,3-benzodioxolan-5-yl]-3-ethylurea | m.p. 144–145° C. |
| 1-[2-(4-methylphenyl)-1,3-benzodioxolan-5-yl]-3-methylurea | m.p. 177–180° C. |
| 1-[2-(4-chlorophenyl)-2-methyl-1,3-benzodioxolan-5-yl]-3-methyl-3-(1-methyl-2-propinyl)-urea | m.p. 154–155° C. |
| 1-[2-(4-chlorophenyl)-2-methyl-1,3-benzodioxolan-5-yl]-3-isoproyl- | |

| Compound | Physical Constants |
|---|---|
| urea | m.p. 153–154° C. |
| 1-[2-(4-chlorophenyl)-2-methyl-1,3-benzodioxolan-5-yl]-3-methoxy-3-methylurea | m.p. 115–117° C. |
| 1-[2-(4-methylphenyl)-1,3-benzodioxolan-5-yl]-3,3-dimethylurea | m.p. 118–120° C. |
| 1-(2-chloromethyl-2-methyl-1,3-benzodioxolan-5-yl)-3-ethylurea | m.p. 139–141° C. |
| 1-(2-chloromethyl-2-methyl-1,3-benzodioxolan-5-yl)-3-butylurea | m.p. 112–113° C. |
| 1-(2-chloromethyl-2-methyl-1,3-benzodioxolan-5-yl)-3-cyclopropyl-urea | m.p. 163–164° C. |
| 1-(2-chloromethyl-2-methyl-1,3-benzodioxolan-5-yl)-3-(1,1-dimethyl-2-propinyl)-urea | m.p. 143–145° C. |
| 1-(2-chloromethyl-2-phenyl-1,3-benzodioxolan-5-yl)-3,3-dimethyl-urea | m.p. 181–183° C. |
| 1-(2-chloromethyl-2-phenyl-1,3-benzodioxolan-5-yl)-3-methyoxy-3-methylurea | m.p. 122–123° C. |
| 1-(2-chloromethyl-2-phenyl-1,3-benzodioxolan-5-yl)-3-(1,1-dimethyl-2-propinyl)-urea | m.p. 169–171° C. |
| 1-(2-chloromethyl-2-phenyl-1,3-benzodioxolan-5-yl)-3-isopropyl-urea | m.p. 145–147° C. |
| 1-(2-chloromethyl-2-phenyl-1,3-benzodioxolan-5-yl)-3-(1-methyl-2-propinyl)-urea | m.p. 163–164° C. |
| 1-(2-methyl-2-phenoxymethyl-1,3-benzodioxolan-5-yl)-3,3-dimethyl-urea | m.p. 133–135° C. |
| 1-(2-methyl-2-phenoxymethyl-1,3-benzodioxolan-5-yl)-3-methoxy-3-methylurea | m.p. 78–80° C. |
| 1-(1,3-benzodioxolan-5-yl)-3,3-dimethylurea | m.p. 128–130° C. |
| 1-[2-(2,6-dichlorophenyl)-1,3-benzodioxolan-5-yl]-3,3-dimethyl-urea | m.p. 191–193° C. |
| 1-[2-(2,6-dichlorophenyl)-1,3-benzodioxolan-5-yl]-3-methoxy-3-methylurea | m.p. 177–178° C. |
| 1-[2-(4-chlorophenyl)-1,3-benzodioxolan-5-yl]-3-(1-methyl-2-propinyl)-3-methylurea | m.p. 145–147° C. |
| 1-[2-(4-chlorophenyl)-1,3-benzodioxolan-5-yl]-3-cyclopropyl-urea | m.p. 242–243° C. |
| 1-[2-(3,4-dichlorophenyl)-1,3-benzodioxolan-5-yl]-3-cyclopropyl-urea | m.p. 202–204° C. |
| 1-[2-(4-chlorophenyl)-1,3-benzodioxolan-5-yl]-3,3-dimethylurea | m.p. 115–118° C. |
| 1-(1,3-benzodioxolan-5-yl)-3-methoxy-3-methylurea | $n_D^{20}$: 1.5643 |
| 1-[2-(4-chlorophenyl)-1,3-benzodioxolan-5-yl]-3-(1,1-dimethyl-2-propinyl)-urea | m.p. 120–122° C. |
| 1-[2-(3,4-dichlorophenyl)-1,3-benzodioxolan-5-yl]-3-(1,1-dimethyl-2-propinyl)-urea | m.p. 125–127° C. |
| 1-[2-(4-chlorophenyl)-2-methyl-1,3-benzodioxolan-5-yl]-3,3-dimethylurea | m.p. 142–144° C. |

The benzodioxolan derivatives of the invention are colorless, non-smelling, oily or crystalline compounds which have a good solubility in acetic acid ethylester, acetone and alcohol. Part of them are only moderately soluble in benzene and they are practically insoluble in saturated hydrocarbons and water.

USE

The following examples will further illustrate the activity and uses of the benzodioxolan derivatives of the invention.

EXAMPLE 3

The benzodioxolan derivatives listed in the following Table I were applied by spraying to the test plants also listed in Table I in an amount of 5 kg of active agent per about 2.5 acres. The compounds were suspended in 500 liter of water per about 2.5 acres. The application was effected in a hot house in a preemergence and postemergence application.

Three weeks after the treatment the results were evaluated on a scale going from 0 = no effect, to 4 = total destruction of the plants.

As appears from the table, in most cases a destruction of the test plants was accomplished.

TABLE I

| Compounds of the Invention | Preemergence mustard | Preemergence tomato | Postemergence mustard | Postemergence tomato |
|---|---|---|---|---|
| 1-(2,2-dimethyl-1,3-benzodioxolan-5-yl)-3-methylurea | 4 | 4 | 4 | 4 |
| 1-(2,2-dimethyl-1,3-benzodioxolan-5-yl)-3,3-dimethylurea | 4 | 4 | 4 | 4 |
| 1-(2-isobutyl-2-methyl-1,3-benzodioxolan 5-yl)-3-methylurea | 4 | 4 | 4 | 4 |
| 1-(2-isobutyl-2-methyl-1,3-benzodioxolan-5-yl)-3,3-dimethylurea | 4 | 4 | 4 | 4 |
| 1-(1,3-benzodioxolan-(2-spirocyclohexane)-5-yl)-3,3-dimethylurea | 4 | 4 | 4 | 4 |
| 1-(1,3-benzodioxolan-(2-spirocyclohexane)-5-yl)-3-methylurea | 4 | 3 | 4 | 1 |
| 1-(1,3-benzodioxolan-(2-spirocyclopentane)-5-yl)-3,3-dimethylurea | 4 | 4 | 4 | 4 |
| 1-(1,3-benzodioxolan-(2-spirocyclopentane)-5-yl)-3-methylurea | 4 | 3 | 4 | 1 |
| 1-(2,2- diethyl-1,3-benzodioxolan-5-yl)-3-methylurea | 4 | 3 | 4 | 4 |
| 1-(2,2-diethyl-1,3-benzodioxolan-5-yl)-3,3-dimethylurea | 3 | 3 | 4 | 4 |
| 1-(2-methyl-2-pentyl-1,3-benzodioxolan-5-yl)-3,3-dimethylurea | 3 | 4 | 4 | 4 |
| 1-(2-methyl-2-pentyl-1,3-benzodioxolan-5-yl)-3-methylurea | 0 | 0 | 4 | 4 |
| 1-(2-isopropyl-1,3-benzodioxolan-5-yl)-3- | | | | |

TABLE I-continued

| Compounds of the Invention | Application: | | | |
|---|---|---|---|---|
| | Preemergence | | Postemergence | |
| | mustard | tomato | mustard | tomato |
| methylurea | 4 | 4 | 4 | 4 |
| 1-(2,2-dipropyl-1,3-benzodioxolan-5-yl)-3,3-dimethylurea | 0 | 2 | 3 | 4 |
| 1-(2,2-dimethyl-1,3-benzodioxolan-5-yl)-3-butylurea | 4 | 4 | 4 | 4 |
| 1-(2,2-dimethyl-1,3-benzodioxolan-5-yl)-3-tert.-butylurea | 3 | 4 | 4 | 4 |
| 1-(2-isopropyl-1,3-benzodioxolan-5-yl)-3,3-dimethylurea | 4 | 4 | 4 | 4 |
| 1-(2-methyl-2-nonyl-1,3-benzodioxolan-5-yl)-3,3-dimethylurea | 0 | 0 | 4 | 4 |
| 1-(2-methyl-2-nonyl-1,3-benzodioxolan-5-yl)-3-methylurea | 0 | 0 | 4 | 3 |
| 1-(2-methyl-2-propyl-1,3-benzodioxolan-5-yl)-3,3-dimethylurea | 4 | 4 | 4 | 4 |
| 1-(2-ethyl-2-methyl-1,3-benzodioxolan-5-yl)-3-ethylurea | 1 | 1 | 2 | 4 |
| 1-(2,2-dimethyl-1,3-benzodioxolan-5-yl)-3-ethylurea | 2 | 2 | 4 | 4 |
| 1-(2-methyl-2-propyl-1,3-benzodioxolan-5-yl)-3-methylurea | 4 | 4 | 4 | 4 |
| 1-(2-isopropyl-2-methyl-1,3-benzodioxolan-5-yl)-3,3-dimethylurea | 4 | 3 | 4 | 4 |
| 1-(2-isopropyl-2-methyl-1,3-benzodioxolan-5-yl)-3-methylurea | 4 | 3 | 4 | 4 |
| 1-(2-ethyl-2-methyl-1,3-benzodioxolan-5-yl)-3,3-dimethylurea | 4 | 4 | 4 | 4 |
| 1-(2-ethyl-2-methyl-1,3-benzodioxolan-5-yl)-3-methylurea | 4 | 4 | 4 | 4 |
| 1- 2-methyl-2-phenyl-1,3-benzodioxolan-5-yl)-3,3-dimethylurea | 4 | 4 | 4 | 4 |
| 1-(2-methyl-2-phenyl-1,3-benzodioxolan-5-yl)-3-methylurea | 4 | 4 | 4 | 4 |
| 1-(2-chloromethyl-2-methyl-1,3-benzodioxolan-5-yl)-3,3-dimethylurea | 4 | 4 | 4 | 4 |
| 1-(2-chloromethyl-2-methyl-1,3-benzodioxolan-5-yl)-3-methylurea | 4 | 4 | 4 | 4 |
| 1-(2-ethyl-2,7-dimethyl-1,3-benzodioxolan-5-yl)-3,3-dimethylurea | 4 | 4 | 4 | 4 |
| 1-(2-ethyl-2,7-dimethyl-1,3-benzodioxolan-5-yl)-3-methylurea | 4 | 4 | 4 | 4 |
| 1-(2-chloromethyl-2,7-dimethyl-1,3-benzodioxolan-5-yl)-3-methylurea | 4 | 4 | — | 3 |
| 1-(2-chloromethyl-2-methyl-1,3-benzodioxolan-5-yl)-3-methoxy-3-methylurea | 4 | 4 | 4 | 4 |
| 1-(2-chloromethyl-2-methyl-1,3-benzodioxolan-5-yl)-3-methyl-3-(1-methyl-2-propinyl)-urea | 4 | 4 | 4 | — |
| 1-(2,2-dimethyl-1,3-benzodioxolan-5-yl)-3-methoxy-3-methylurea | 4 | 4 | 4 | 4 |
| 1-(2-phenyl-1,3-benzodioxolan-5-yl)-3-methylurea | — | — | 4 | 4 |
| 1-[2-(4-chlorophenyl)-2-methyl-1,3-benzodioxolan-5-yl]-3-methylurea | — | — | 4 | 4 |
| 1-[2-(4-chlorophenyl)-2-methyl-1,3-benzodioxolan-5-yl]-3-ethylurea | — | — | 4 | 4 |
| 1-[2-(4-methylphenyl)-1,3-benzodioxolan-5-yl]-3-methylurea | — | — | 4 | 4 |
| 1-[2-(4-chlorophenyl)-2-methyl-1,3-benzodioxolan-5-yl]-3-methyl-3-(1-methyl-2-propinyl)-urea | — | — | 4 | 4 |
| 1-[2-(4-chlorophenyl)-2-methyl-1,3-benzodioxolan-5-yl]-3-isopropyl-urea | — | — | — | 4 |
| 1-[2-(4-chlorophenyl)-2-methyl-1,3-benzodioxolan-5-yl]-3-methoxy-3-methylurea | — | — | 4 | 4 |
| 1-[2-(4-methylphenyl)-1,3-benzodioxolan-5-yl]-3,3-dimethylurea | 4 | 4 | 4 | 4 |
| 1-(2-chloromethyl-2-methyl-1,3-benzodioxolan-5-yl)-3-ethylurea | 4 | 4 | 4 | 4 |
| 1-(2-chloromethyl-2-methyl-1,3-benzodioxolan-5-yl)-3-butylurea | 4 | 4 | 4 | 4 |
| 1-(2-chloromethyl-2-methyl-1,3-benzodioxolan-5-yl)-3-cyclopropyl-urea | 4 | 4 | 4 | 4 |
| 1-(2-chloromethyl-2-methyl-1,3-benzodioxolan-5-yl)-3-(1,1-dimethyl-2-propinyl)-urea | 4 | 4 | 4 | — |

TABLE I-continued

| Compounds of the Invention | Application: | | | |
|---|---|---|---|---|
| | Preemergence | | Postemergence | |
| | mustard | tomato | mustard | tomato |
| 1-(2-chloromethyl-2-phenyl-1,3-benzodioxolan-5-yl)-3-methoxy-3-methylurea | — | — | 4 | 4 |
| 1-(2-chloromethyl-2-phenyl-1,3-benzodioxolan-5-yl)-3-(1-methyl-2-propinyl)-urea | — | — | 4 | — |
| 1-(1,3-benzodioxolan-5-yl)-3,3-dimethylurea | 4 | 4 | 4 | 4 |
| 1-[2-(2,6-dichlorophenyl)-1,3-benzodioxolan-5-yl]-3,3-dimethylurea | — | — | 4 | 4 |
| 1-[2-(2,6-dichlorophenyl)-1,3-benzodioxolan-5-yl]-3-methoxy-3-methylurea | — | — | 4 | 4 |
| 1-[2-(4-chlorophenyl)-1,3-benzodioxolan-5-yl]-3-(1-methyl-2-propinyl)-3-methylurea | — | — | 4 | 3 |
| 1-[2-(4-chlorophenyl)-1,3-benzodioxolan-5-yl]-3-cyclopropyl-urea | — | — | 4 | 4 |
| 1-[2-(3,4-dichlorophenyl)-1,3-benzodioxolan-5-yl]-3-cyclopropyl-urea | — | — | 4 | 4 |
| 1-[2-(4-chlorophenyl)-1,3-benzodioxolan-5-yl]-3,3-dimethylurea | 4 | 3 | 4 | 4 |
| 1-(1,3-benzodioxolan-5-yl)-3-methoxy 3-methylurea | 4 | 3 | 3 | 3 |
| 1-[2-(4-chlorophenyl)-1,3-benzodioxolan-5-yl]-3-(1,1-dimethyl-2-propinyl)-urea | — | — | 4 | 3 |
| 1-[2-(3,4-dichlorophenyl)-1,3-benzodioxolan-5-yl]-3-(1,1-dimethyl-2-propinyl)-urea | — | — | 4 | 4 |
| 1-[2-(4-chlorophenyl)-2-methyl-1,3-benzodioxolan-5-yl]-3,3-dimethylurea | 4 | 4 | 4 | 4 |

An analogous activity was established in the following compounds:
1-(2-chloromethyl-2-phenyl-1,3-benzodioxolan-5-yl)-3,3-dimethylurea.
1-(2-chloromethyl-2-phenyl-1,3-benzodioxolan-5-yl)-3-(1,1-dimethyl-2-propinyl)-urea.
1-(2-chloromethyl-2-phenyl-1,3-benzodioxolan-5-yl)-3-isopropylurea.
1-(2-methyl-2-phenoxymethyl-1,3-benzodioxolan-5-yl)-3,3-dimethylurea.
1-(2-methyl-2-phenoxymethyl-1,3-benzodioxolan-5-yl)-3-methoxy-3-methylurea.

EXAMPLE 4

The plants listed in the following Example 2 were treated in a hot house in a preemergence application with the compounds also listed in the table in amounts of 1 kg of active agent per about 2.5 acres. The compounds for this purpose were applied in a uniform manner to the ground in the form of aqueous suspensions in 500 liter water per about 2.5 acres.

The results after three weeks from the treatment showed that the compounds of the invention had a higher activity than the comparison compound.

TABLE II

| Compounds of the Invention | Stellaria m. | Senecio v. | Matricaria ch. | Lamium a. | Centaurea c. | Amaranthus r. | Chrysanthemum m. | Ipomea p. | Polygonum l. | Avena f. | Alopecurus m. | Echinochloa c.g. | Setaria i. | Digitaria s. | Sorghum h. | Poa a. |
|---|---|---|---|---|---|---|---|---|---|---|---|---|---|---|---|---|
| 1-(2-methyl-2-phenyl-1,3-benzodioxolan-5-yl)-3,3-dimethylurea | 0 | 0 | 1 | 0 | 0 | 0 | 0 | 0 | 5 | 0 | 2 | 3 | 3 | 1 | 5 | 3 |
| 1-(2-chloromethyl-2-methyl-1,3-benzodioxolan-5-yl)-3,3-dimethylurea | 0 | 0 | 0 | 0 | 0 | 0 | 0 | 0 | 0 | 0 | 0 | 0 | 0 | 0 | 8 | 0 |
| Comparison compound 1-[4-(4-Chlorophenoxy)-phenyl]- | | | | | | | | | | | | | | | | |

TABLE II-continued

| Compounds of the Invention | Stellaria m. | Senecio v. | Matricaria ch. | Lamium a. | Centaurea c. | Amaranthus r. | Chrysanthemum m. | Ipomea p. | Polygonum l. | Avena f. | Alopecurus m. | Echinochloa c.g. | Setaria i. | Digitaria s. | Sorghum h. | Poa a. |
|---|---|---|---|---|---|---|---|---|---|---|---|---|---|---|---|---|
| 3,3-dimethylurea | 0 | 0 | 0 | 3 | 2 | 0 | 2 | 0 | 5 | 0 | 2 | 7 | 3 | 1 | 8 | 3 |
| Untreated | 10 | 10 | 10 | 10 | 10 | 10 | 10 | 10 | 10 | 10 | 10 | 10 | 10 | 10 | 10 | 10 |

Scale
0 = total destruction of plant
= no injury to plant

EXAMPLE 5

The plants listed in the Table III were treated in a hot house and in a preemergence application with the compounds also listed in the table in amounts of 1 kg of active agent per about 2.5 acres. For this purpose the compounds were applied in a uniform manner to the ground in the form of aqueous suspensions in 500 liter of water per about 2.5 acres.

The results after three weeks from the treatment showed that the compounds of the invention had a higher selectivity than the comparison compound.

TABLE III

| Compounds of the Invention | cotton | peanuts | soybean | sunflowers | potatoes | peas | maize | wheat | barley | rice | seedsorghum |
|---|---|---|---|---|---|---|---|---|---|---|---|
| 1-(2-methyl-2-phenyl-1,3-benzodioxolan-5-yl)-3,3-dimethyulurea | 10 | 10 | 10 | 8 | 10 | 10 | 10 | 10 | 10 | 10 | 8 |
| 1-(2-chloromethyl-2-methyl-1,1,3-benzodioxolan-5-yl)-3,3-dimethylurea | — | 10 | — | — | 10 | 10 | 10 | 8 | 8 | 10 | 5 |
| Comparison compound | | | | | | | | | | | |
| 1-[4-(4-chlorophenoxy)-phenyl]-3,3-dimethylurea | 1 | 10 | 0 | 0 | 3 | 2 | 4 | 0 | 0 | 1 | 0 |
| Untreated | 10 | 10 | 10 | 10 | 10 | 10 | 10 | 10 | 10 | 10 | 10 |

Scale
0 = total destruction of plant
10 = no injury to plant

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Benzodioxolan derivatives of the formula

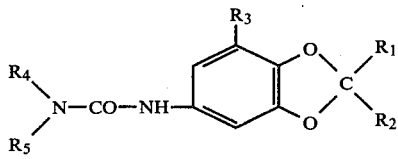

in which $R_1$ and/or $R_2$ are hydrogen, monohaloalkyl of 1 to 3 carbon atoms, dihaloalkyl of 1 to 3 carbon atoms or phenyl, or are phenyl or furyl substituted in one or two places by methyl, halogen, cyano, or methoxy, or wherein if one of $R_1$ or $R_2$ is methyl, the other must be nonyl or as before defined, excluding hydrogen, or wherein $R_1$ and $R_2$ together with one adjoining carbon atom form a cycloaliphatic hydrocarbon residue of 5 to 6 carbon atoms, and in which $R_3$ is hydrogen or methyl, $R_4$ is alkyl of 1 to 4 carbon atoms, alkenyl of 2 to 4 carbon atoms, alkinyl of 2 to 4 carbon atoms or methoxy, and wherein $R_5$ is hydrogen or methyl, provided that if $R_1$ and $R_2$ are both hydrogen, $R_4$ must be alkenyl or alkinyl as defined above, or must be methoxy.

2. The benzodioxalan derivative of claim 1 in which halogen in mono- or di-halogenoalkyl or in halogen substituted phenyl is chloro.

3. The compound of claim 1 which is 1-(2-chloromethyl-2-methyl-1,3-benzodioxolan-5-yl)-3-methylurea.

4. The compound of claim 1 which is 1-(2-phenyl-1,3-benzodioxolan-5-yl)-3,3-dimethylurea.

5. The compound of claim 1 which is 1-(1,3-benzodioxolan-(2-spirocyclohexane)-5-yl)-3,3-dimethylurea.

6. The compound of claim 1 which is 1-(1,3-benzodioxolan-(2-spirocyclohexane)-5-yl)-3-methylurea.

7. The compound of claim 1 which is 1-(1,3-benzodioxolan-(2-spirocyclopentane)-5-yl)-3,3-dimethylurea.

8. The compound of claim 1 which is 1-(1,3-benzodioxolan-(2-spirocyclopentane)-5-yl)-3-methylurea.

9. The compound of claim 1 which is 1-(2-methyl-2-nonyl-1,3-benzodioxolan-5-yl)-3,3-dimethylurea.

10. The compound of claim 1 which is 1-(2-methyl-2-nonyl-1,3-benzodioxolan-5-yl)-3-methylurea.

11. The compound of claim 1 which is 1-(2-methyl-2-phenyl-1,3-benzodioxolan-5-yl)-3,3-dimethylurea.

12. The compound of claim 1 which is 1-(2-methyl-2-phenyl-1,3-benzodioxolan-5-yl)-3-methylurea.

13. The compound of claim 1 which is 1-(2-chloromethyl-2-methyl-1,3-benzodioxolan-5-yl-3,3-dimethylurea.

14. The compound of claim 1 which is 1-(2-chloromethyl-2,7-dimethyl-1,3-benzodioxolan-5-yl)-3-methylurea.

15. The compound of claim 1 which is 1-(2-chloromethyl-2-methyl-1,3-benzodioxolan-5-yl)-3-methoxy-3-methyl-urea.

16. The compound of claim 1 which is 1-(2-chloromethyl-2-methyl-1,3-benzodioxolan-5-yl)-3-methyl-3-(1-methyl-2-propinyl)-urea.

17. The compound which is 1-(2,2-dimethyl-1,3-benzodioxolan-5-yl)-3-methoxy-3-methyl-urea.

18. The compound of claim 1 which is 1-(2-phenyl-1,3-benzodioxolan-5-yl)-3-methylurea.

19. The compound of claim 1 which is 1-[2-(4-chlorophenyl)-2-methyl-1,3-benzodioxolan-5-yl]-3-methylurea.

20. The compound of claim 1 which is 1-[2-(4-chlorophenyl)-2-methyl-1,3-benzodioxolan-5-yl]-3-ethyl-urea.

21. The compound of claim 1 which is 1-[2-(4-methylphenyl)-1,3-benzodioxolan-5-yl]-3-methyl-urea.

22. The compound of claim 1 which is 1-[2-(4-chlorophenyl)-2-methyl-1,3-benzodioxolan-5-yl]-3-methyl-3-(1-methyl-2-propinyl)-urea.

23. The compound of claim 1 which is 1[2-(4-chlorophenyl)-2-methyl-1,3-benzodioxolan-5-yl]-3-isopropylurea.

24. The compound of claim 1 which is 1-[2-(4-chlorophenyl)-2-methyl-1,3-benzodioxolan-5-yl]-3-methoxy-3-methylurea.

25. The compound of claim 1 which is 1-[2-(4-methylphenyl)-1,3-benzodioxolan-5-yl]-3,3-dimethyl-urea.

26. The compound of claim 1 which is 1-(2-chloromethyl-2-methyl-1,3-benzodioxolan-5-yl)-3-ethyl-urea.

27. The compound of claim 1 which is 1-(2-chloromethyl-2-methyl-1,3-benzodioxolan-5-yl)-3-butyl-urea.

28. The compound of claim 1 which is 1-(2-chloromethyl-2-methyl-1,3-benzodioxolan-5-yl)-3-cyclopropyl-urea.

29. The compound of claim 1 which is 1-(2-chloromethyl-2-methyl-1,3-benzodioxolan-5-yl)-3-(1,1-dimethyl-2-propinyl)-urea.

30. The compound of claim 1 which is 1-(2-chloromethyl-2-phenyl-1,3-benzodioxolan-5-yl)-3,3-dimethyl-urea.

31. The compound of claim 1 which is 1-(2-chloromethyl-2-phenyl-1,3-benzodioxolan-5-yl)-3-methoxy-3-methyl-urea.

32. The compound of claim 1 which is 1-(2-chloromethyl-2-phenyl-1,3-benzodioxolan-5-yl)-3-(1,1-dimethyl-2-propinyl)-urea.

33. The compound of claim 1 which is 1-(2-chloromethyl-2-phenyl-1,3-benzodioxolan-5-yl)-3-isopropyl-urea.

34. The compound of claim 1 which is 1-(2-chloromethyl-2-phenyl-1,3-benzodioxolan-5-yl)-3-(1-methyl-2-propinyl)-urea.

35. The compound of claim 1 which is 1-(2-methyl-2-phenoxymethyl-1,3-benzodioxolan-5-yl)-3,3-dimethylurea.

36. The compound of claim 1 which is 1-(2-methyl-2-phenoxymethyl-1,3-benzodioxolan-5-yl)-3-methoxy-3-methylurea.

37. The compound of claim 1 which is 1-[2-(2,6-dichlorophenyl)-1,3-benzodioxolan-5-yl]-3,3-dimethylurea.

38. The compound of claim 1 which is 1-[2-(2,6-dichlorophenyl)-1,3-benzodioxolan-5-yl]-3-methoxy-3-methylurea.

39. The compound of claim 1 which is 1-[2-(4-chlorophenyl)-1,3-benzodioxolan-5-yl]-3-1-methyl-2-propinyl)-3-methylurea.

40. The compound of claim 1 which is 1-[2-(4-chlorophenyl)-1,3-benzodioxolan-5-yl]-3-cyclopropyl-urea.

41. The compound of claim 1 which is 1-[2-(3,4-dichlorophenyl)-1,3-benzodioxolan-5-yl]-3-cyclopropyl-urea.

42. The compound of claim 1 which is 1-[2-(4-chlorophenyl)-1,3-benzodioxolan-5-yl]-3,3-dimethylurea.

43. The compound of claim 1 which is 1-(1,3-benzodioxolan-5-yl)-3-methoxy-3-methylurea.

44. The compound of claim 1 which is 1-[2-(4-chlorophenyl)-1,3-benzodioxolan-5-yl]-3-(1,1-dimethyl-2-propinyl)-urea.

45. The compound of claim 1 which is 1-[2-(3,4-dichlorophenyl)-1,3-benzodioxolan-5-yl]-3-(1,1-dimethyl-2-propinyl)-urea.

46. The compound of claim 1 which is 1-[2-(4-chlorophenyl)-2-methyl-1,3-benzodioxolan-5-yl]-3,3-dimethyl-urea.

* * * * *